(12) United States Patent  
Tewari et al.

(10) Patent No.: US 8,841,444 B2  
(45) Date of Patent: Sep. 23, 2014

(54) PROCESS FOR THE PREPARATION OF CARBAPENEM COMPOUNDS

(75) Inventors: Neera Tewari, Gurgaon (IN); Shailendra Kumar Singh, Gurgaon (IN); Brij Kishore Mishra, Bilaspur (IN); Saraswati Rani, Moradabad (IN)

(73) Assignee: Ranbaxy Laboratories Limited, New Delhi (IN)

( * ) Notice: Subject to any disclaimer, the term of this patent is extended or adjusted under 35 U.S.C. 154(b) by 724 days.

(21) Appl. No.: 13/056,837

(22) PCT Filed: Jul. 30, 2009

(86) PCT No.: PCT/IB2009/053332  
§ 371 (c)(1),  
(2), (4) Date: May 25, 2011

(87) PCT Pub. No.: WO2010/013223  
PCT Pub. Date: Feb. 4, 2010

(65) Prior Publication Data  
US 2011/0224426 A1   Sep. 15, 2011

(30) Foreign Application Priority Data  
Jul. 30, 2008  (IN) .......................... 1808/DEL/2008

(51) Int. Cl.  
*C07D 477/20* (2006.01)  
*C07D 477/04* (2006.01)

(52) U.S. Cl.  
CPC .................................. *C07D 477/04* (2013.01)  
USPC ....................................................... 540/350

(58) Field of Classification Search  
CPC ..................................................... C07D 477/20  
See application file for complete search history.

(56) References Cited

U.S. PATENT DOCUMENTS

| 4,260,543 A | 4/1981 | Miller ....................... 260/245.2 T |
| 4,262,010 A | 4/1981 | Christensen et al. ......... 424/274 |

(Continued)

FOREIGN PATENT DOCUMENTS

| EP | 0 072 710 | 2/1986 | ............ C07D 487/04 |
| EP | 0243686 A2 * | 11/1987 | ............ C07D 487/04 |

(Continued)

OTHER PUBLICATIONS

Nishino et al., "Practical Large-Scale Synthesis of Doripenem: A Novel 1β-Methylcarbapenem Antibiotic", *Organic Process Research & Development*, 7(6):846-850 (2003).

(Continued)

*Primary Examiner* — Andrew D Kosar  
*Assistant Examiner* — John S Kenyon

(57) ABSTRACT

The present invention relates to a process for the preparation of carbapenem compound of Formula (I), wherein $P_1$ is hydrogen or a carboxyl protecting group, $P_3$ is hydrogen or a hydroxyl protecting group, $R_1$ is $C_{1-3}$ alkyl, and A is selected from a group consisting of a) Formula (II), b) Formula (III), c) Formula (IV), d) Formula (V), e) Formula (VI), f) Formula (VII), wherein $P_2$ is hydrogen or an amino protecting group, $R_2$ and $R_3$ may be same or different and are hydrogen, $C_{1-5}$ alkyl, optionally substituted aryl, or optionally substituted heteroaryl, and $X_1$ is O or S, or its stereoisomers, or salts thereof.

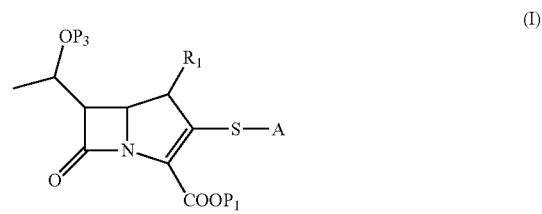

(I)

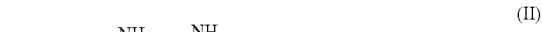

(II)

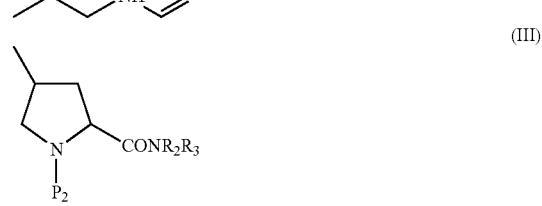

(III)

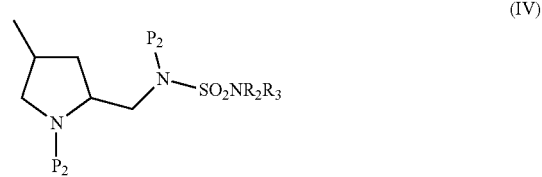

(IV)

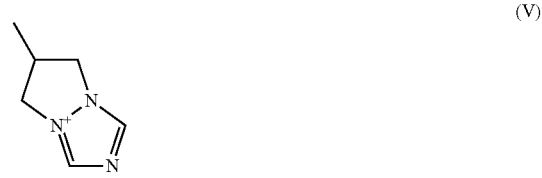

(V)

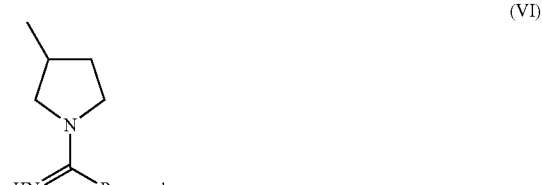

(VI)

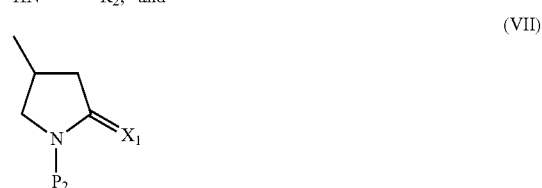

(VII)

8 Claims, No Drawings

(56) References Cited

U.S. PATENT DOCUMENTS

| | | | |
|---|---|---|---|
| 4,273,709 A | 6/1981 | Christensen et al. | 260/239 A |
| 4,282,148 A | 8/1981 | Liu et al. | 260/239 A |
| 4,312,871 A | 1/1982 | Christensen et al. | 424/263 |
| 4,350,631 A | 9/1982 | Christensen et al. | 260/245.2 T |
| 4,360,684 A | 11/1982 | Cvetovich et al. | 549/291 |
| 4,499,278 A | 2/1985 | Melillo et al. | 548/240 |
| 4,683,296 A | 7/1987 | Ueda et al. | 539/558 |
| 4,833,167 A | 5/1989 | Christensen et al. | 514/210 |
| 4,888,344 A | 12/1989 | Sunagawa et al. | 514/210 |
| 4,918,184 A | 4/1990 | Nagao et al. | 540/200 |
| 4,943,569 A | 7/1990 | Sunagawa | 514/210 |
| 4,990,613 A | 2/1991 | Kumagai et al. | 540/350 |
| 5,075,437 A | 12/1991 | Nakai et al. | 540/200 |
| 5,104,984 A | 4/1992 | Salzmann et al. | 540/200 |
| 5,231,179 A | 7/1993 | Terashima et al. | 540/200 |
| 5,260,438 A | 11/1993 | Horikawa et al. | 540/302 |
| 5,317,016 A | 5/1994 | Nishitani et al. | 514/210 |
| 5,414,081 A | 5/1995 | Horikawa et al. | 540/302 |
| 5,424,422 A | 6/1995 | Sunagawa et al. | 540/200 |
| 5,442,057 A | 8/1995 | Decamp et al. | 540/302 |
| 5,478,820 A | 12/1995 | Betts et al. | 514/210 |
| 5,493,018 A | 2/1996 | Liu et al. | 540/302 |
| 5,574,152 A | 11/1996 | Miura et al. | 540/200 |
| 5,578,722 A | 11/1996 | Sunagawa et al. | 540/302 |
| 5,580,976 A | 12/1996 | Kume et al. | 540/200 |
| 5,587,474 A | 12/1996 | Kondo et al. | 540/350 |
| 5,703,234 A | 12/1997 | Iwasaki et al. | 544/50 |
| 5,731,431 A | 3/1998 | Nakagawa et al. | 540/200 |
| 5,792,861 A | 8/1998 | Hara et al. | 540/200 |
| 5,973,142 A | 10/1999 | Yasuda et al. | 540/200 |
| 6,011,150 A | 1/2000 | Iwasaki et al. | 540/200 |
| 6,080,854 A | 6/2000 | Chung et al. | 540/200 |
| 6,162,911 A | 12/2000 | Ball et al. | 540/200 |
| 6,340,751 B1 | 1/2002 | Saito et al. | 540/200 |
| 6,858,727 B2 | 2/2005 | Lee et al. | 540/200 |
| 6,867,297 B1 | 3/2005 | Ishiguro et al. | 540/200 |

FOREIGN PATENT DOCUMENTS

| | | | | |
|---|---|---|---|---|
| EP | 0326640 A1 * | 8/1989 | | C07D 487/04 |
| EP | 0 444 889 | 9/1991 | | C07D 477/00 |
| EP | 0 300 657 | 3/1993 | | C07D 205/08 |
| EP | 0 597 423 | 3/2002 | | C07D 401/06 |
| JP | 62-169781 | 7/1987 | | C07D 413/06 |
| JP | 07-005590 | 11/1987 | | C07D 413/06 |
| JP | 63-112558 | 5/1988 | | C07D 205/08 |
| JP | 2510860 | 8/1988 | | C07D 205/08 |
| JP | 63-284176 | 11/1988 | | C07D 487/04 |
| JP | 2592110 | 3/1990 | | C07D 477/00 |
| JP | 02-178262 | 7/1990 | | C07D 205/08 |
| JP | 04-117382 | 4/1992 | | C07D 477/00 |
| JP | 3080417 | 11/1992 | | C07F 9/572 |
| JP | 04-368365 | 12/1992 | | C07D 205/08 |
| JP | 04-368386 | 12/1992 | | C07D 477/00 |
| JP | 2902178 | 4/1993 | | C07D 205/08 |
| JP | 3219833 | 8/1993 | | C07D 205/08 |
| JP | 06-065195 | 3/1994 | | C07D 205/08 |
| JP | 3479720 | 11/1994 | | C07D 477/00 |
| JP | 07-013058 | 2/1995 | | C07D 205/08 |
| JP | 3388874 | 10/1995 | | C07D 413/06 |
| JP | 08-081439 | 3/1996 | | C07D 205/08 |
| JP | 3761096 | 7/1996 | | C07D 477/00 |
| JP | 08-311092 | 11/1996 | | C07F 9/6561 |
| JP | 08-325261 | 12/1996 | | C07D 403/06 |
| JP | 09-031054 | 2/1997 | | C07D 205/08 |
| JP | 09-031075 | 2/1997 | | C07D 477/00 |
| JP | 09-316071 | 12/1997 | | C07D 403/06 |
| JP | 10-077263 | 3/1998 | | C07D 205/08 |
| JP | 10-087657 | 4/1998 | | C07D 403/06 |
| JP | 2000-007676 | 1/2000 | | C07D 477/00 |
| JP | 2000-044537 | 2/2000 | | C07D 205/08 |
| JP | 2000-044587 | 2/2000 | | C07F 9/6561 |
| JP | 2002-338572 | 11/2002 | | C07D 477/00 |
| JP | 2003-026680 | 1/2003 | | C07D 477/00 |
| JP | 3467265 | 3/2003 | | C07F 7/18 |
| JP | 2003-277390 | 10/2003 | | C07F 7/18 |
| WO | 0 836 607 | 1/1997 | | C07F 7/18 |
| WO | WO 02/20476 | 3/2002 | | |

OTHER PUBLICATIONS

Sunagawa et al., "A Novel Carbapenem Antibiotic, SM-7338 Structure-Activity Relationships", *The Journal of Antibiotics*, 43(5):519-532 (1990).

Matsumura et al., "An Efficient Synthesis of (2S,4S)-2-Substituted 4-Mercaptopyrrolidine Derivatives", *Heterocycles*, 41(1):147-159 (1995).

Shih et al., "Synthetic Carbapenem Antibiotics. I. 1-β-Methylcarbapenem", *Heterocycles*, 21(1):29-41 (1984).

Tewari et al., "Development of a Scalable Process for 1-β-Methyl Azetidinone: A Carbapenem Key Intermediate", *Organic Process Research & Development*, 9(6):827-829 (2005).

Nishino et al., "Practical Large-Scale Synthesis of the 2-Aminomethylpyrrolidin-4-ylthio-Containing Side Chain of the Novel Carbapenem Antibiotic Doripenem", *Organic Process Research & Development*, 7(5):649-654 (2003).

\* cited by examiner

PROCESS FOR THE PREPARATION OF CARBAPENEM COMPOUNDS

FIELD OF THE INVENTION

The present invention relates to process for the preparation of a carbapenem compound of Formula I

FORMULA I

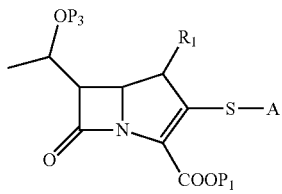

wherein $P_1$ is hydrogen or a carboxyl protecting group, $P_3$ is hydrogen or a hydroxyl protecting group, $R_1$ is $C_{1-3}$ alkyl, and A is selected from a group consisting of a)

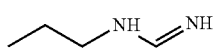

b)

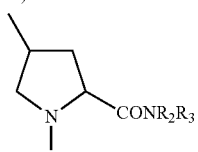

c)

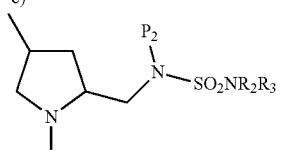

d)

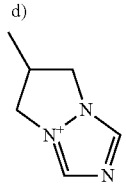

e)

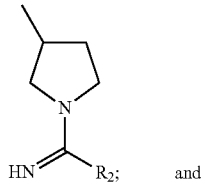

and f)

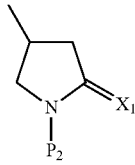

wherein $P_2$ is hydrogen or an amino protecting group, $R_2$ and $R_3$ may be same or different and are hydrogen, $C_{1-5}$ alkyl, optionally substituted aryl, or optionally substituted heteroaryl, and $X_1$ is O or S, or its stereoisomers, or salts thereof.

BACKGROUND OF THE INVENTION

A large number of carbapenem compounds have been prepared and investigated for clinical efficacy. Meropenem, ertapenem, doripenem and biapenem are some of the carbapenem compounds available in the market for treating various bacterial infections. The processes for preparing carbapenem compounds of Formula I and their intermediates are described in several prior art references including U.S. Pat. Nos. 5,424,422; 4,683,296; 4,833,167; 5,104,984; 5,574,152; 5,587,474; 5,260,438; 5,414,081; 6,867,297; 5,792,861; 5,578,722; 5,973,142; 6,080,854; 6,340,751; 6,858,727; 5,231,179; 6,011,150; 5,703,234; 5,580,976; 5,493,018; 5,442,057; 6,162,911; 5,731,431; 4,918,184; and 5,075,437, EP Patent No. 0 300 657131, EP Application No. 0 444 889 A1 and 0 836 607 A1, PCT Publication No. WO 02/020476, Japanese Patent Nos. 2510860; 2592110; 2902178; 3219833; 3388874; 3479720; 3761096; 3080417; and 3467265, Japanese Publication Nos. 07-005590; 63-112558; 02-178262; 04-117382; 04-368365; 04-368386; 06-065195; 2002-338572; 08-081439; 08-325261; 08-311092; 09-031054; 09-316071; 2000-044537; 07-013058; 09-031075; 2000-044587; 2003-026680; 10-077263; 2003-277390; and 2000-007676 A2, Yutaka et al, *Org. Process Res. Dev.* (2003) 7:846-850, Sunagawa et al., *J. Antibiot.* (Tokyo), (1990) 43(5):519-532 and Haruki et al., *Heterocycles,* (1995) 36:145 159 41:147-159.

The carbapenem compounds of Formula I are generally prepared in the prior art by reacting a compound of Formula VIII with a compound of Formula IX

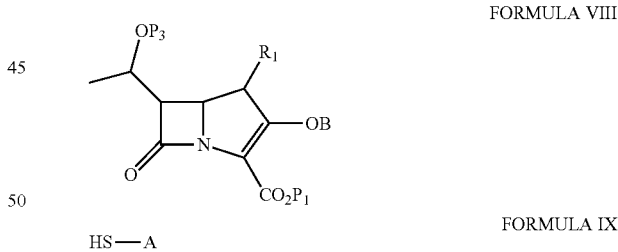

FORMULA VIII

FORMULA IX wherein $R_1$ is $C_{1-3}$ alkyl

B is $—P(O)(OR)_2$ or $—SO_2R$, wherein R is substituted or unsubstituted $C_{1-6}$ alkyl, aralkyl or aryl, $P_1$ is hydrogen or a carboxyl protecting group $P_3$ is hydrogen or a hydroxyl protecting group, and A is as defined in Formula I.

There are several multi-step synthetic routes available in the prior art for preparing the compound of Formula VIII via various azetidinone intermediates. For example, U.S. Pat. No. 4,350,631 provides the following process for the preparation of the compound of Formula VIII.

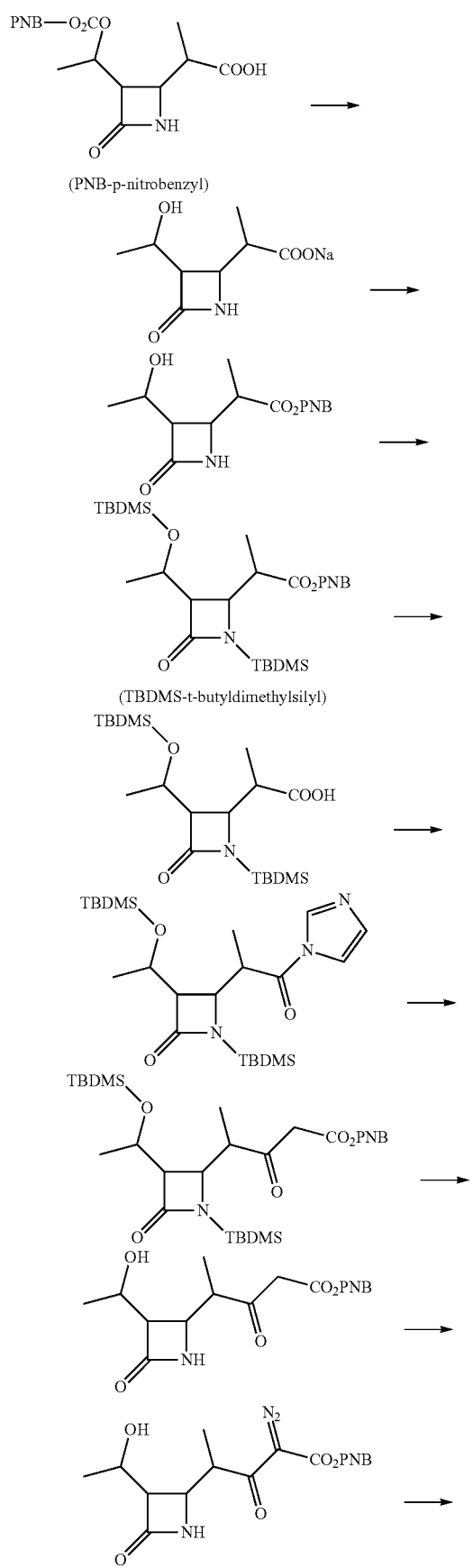

(PNB-p-nitrobenzyl)

(TBDMS-t-butyldimethylsilyl)

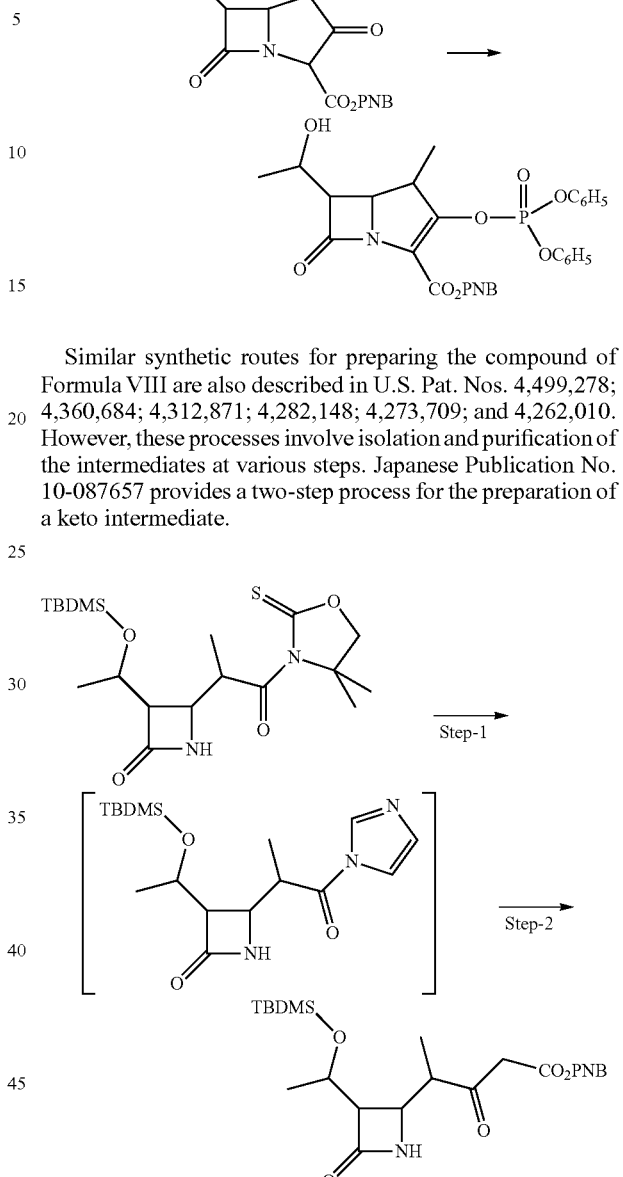

Similar synthetic routes for preparing the compound of Formula VIII are also described in U.S. Pat. Nos. 4,499,278; 4,360,684; 4,312,871; 4,282,148; 4,273,709; and 4,262,010. However, these processes involve isolation and purification of the intermediates at various steps. Japanese Publication No. 10-087657 provides a two-step process for the preparation of a keto intermediate.

Step-1 of the above process described in Japanese Publication No. 10-087657 is carried out in the presence of imidazole, dimethylaminopyridine and ethyl acetate at 60° C. for 4 h. Step-2 is carried out in the presence of magnesium mono-p-nitrobenzyl malonate and ethyl acetate at 50° C. for 2.3 h. However, Japanese Publication No. 10-087657 does not disclose any method to isolate, purify or cyclize further the keto compound obtained in step-2. Japanese Publication No. 10-087657 also does not disclose any specific method to obtain any carbapenem antibiotic from the disclosed process.

SUMMARY OF THE INVENTION

The present inventors have developed an advantageous process to obtain the compound of Formula I, wherein the process eliminates the necessity of isolating the intermediates involved in the preparation of the compound of Formula VIII.

Further, the entire reaction steps of the present process can be carried out at lower temperature conditions compared to the prior art and thereby minimizes the formation of impurities in every step of the process. The present process is efficient to obtain the compound of Formula VIII with a purity of about 99% or above with better yield. Thus, the present process reduces the cost and time involved in preparing carbapenem compounds of Formula I.

The term "protecting group" in the present invention refers to those used in the art and serve the function of blocking the carboxyl, amino or hydroxyl groups while the reactions are carried out at other sites of the molecule. Examples of a carboxyl protecting group include, but not limited to, alkyl, alkenyl, aralkyl, and aryl groups. Examples of hydroxyl and amino protecting groups include, but not limited to, alkylsilyl, alkoxymethyl, aralkyl, acyl, alkoxycarbonyl, alkenyloxycarbonyl and aralkyloxycarbonyl groups.

DETAILED DESCRIPTION OF THE INVENTION

A first aspect of the present invention provides a process for the preparation of the compound of Formula I

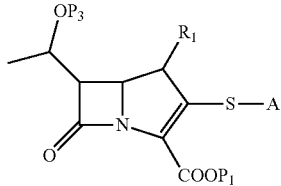

FORMULA I wherein
  $P_1$ is hydrogen or a carboxyl protecting group,
  $P_3$ is hydrogen or a hydroxyl protecting group,
  $R_1$ is $C_{1-3}$ alkyl, and
  A is selected from a group consisting of

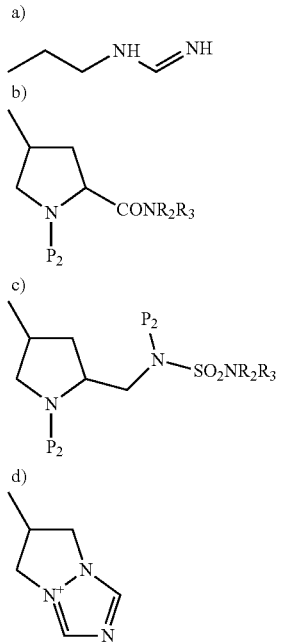

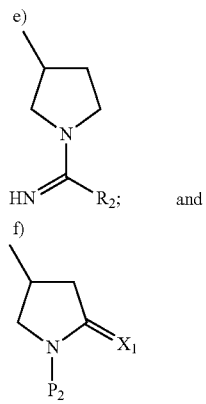

wherein
  $P_2$ is hydrogen or an amino protecting group,
  $R_2$ and $R_3$ may be same or different and are hydrogen, $C_{1-5}$ alkyl, optionally substituted aryl, or optionally substituted heteroaryl, and
  $X_1$ is O or S,
or its stereoisomers, or salts thereof,
wherein the process comprises,
a) reacting a compound of Formula II

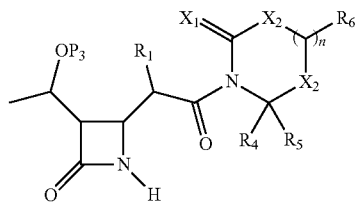

FORMULA II wherein
  $X_1$ is O or S,
  $X_2$ is O, S, $NR_7$ or $C(R_4)R_5$,
  $R_1$ is $C_{1-3}$ alkyl,
  $R_4$ and $R_5$ may be same or different and are
  (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, or
  (ii) $R_4$ and $R_5$ may be joined together to form a $C_{3-18}$ cycloalkyl group, or saturated or partially unsaturated heterocycle having optionally substituted 1 to 4 ring systems, wherein each ring has 3 to 12 ring members and at least one ring member of at least one ring system is N, O or S,
  $R_6$ is
  (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, or (ii) $R_6$ may be joined together with $R_1$ or $R_5$ of $X_2$ to form a $C_{3-18}$ cycloalkyl group, optionally substituted $C_6$-$C_{12}$ aromatic ring or saturated or partially unsaturated heterocycle having optionally substituted 1 to 4 ring systems, wherein each ring has 3 to 12 ring members and at least one ring member of at least one ring system is N, O or S, $R_7$ is hydrogen, $C_{1-18}$ alkyl, $C_{2-48}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, $P_3$ is hydrogen or a hydroxyl protecting group, and n is 0 to 3, and imidazole or carbonyldiimidazole in the presence of an organic solvent to obtain a compound of Formula III

FORMULA III

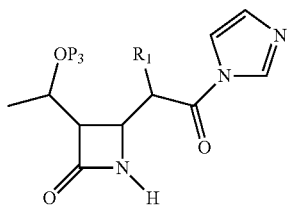

wherein $R_1$ is $C_{1-3}$ alkyl and $P_3$ is hydrogen or a hydroxyl protecting group, b) reacting the compound of Formula III without isolating from the reaction mixture in any solid form and a compound of Formula IV or its magnesium salt, $P_1O_2C-CH_2-CO_2H$  FORMULA IV

wherein $P_1$ is hydrogen or a carboxyl protecting group, to obtain a compound of Formula V

FORMULA V

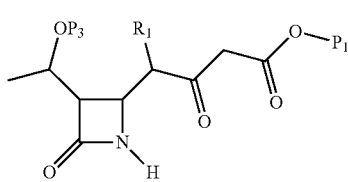

wherein $R_1$ is $C_{1-3}$ alkyl $P_1$ is hydrogen or a carboxyl protecting group and $P_3$ is hydrogen or a hydroxyl protecting group, c) reacting the compound of Formula V without isolating from the reaction mixture in any solid form and an azide to obtain a compound of Formula VI,

FORMULA VI

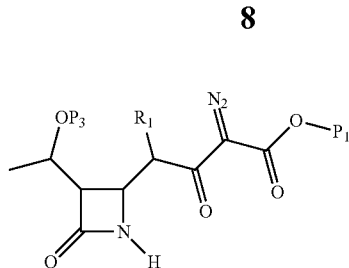

wherein $P_1$, $P_3$ and $R_1$ are as defined in Formula V, d) cyclizing the compound of Formula VI to obtain a compound of Formula VII,

FORMULA VII

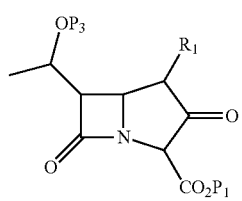

wherein $P_1$, $P_3$ and $R_1$ are as defined in Formula V, e) reacting the compound of Formula VII without isolating from the reaction mixture in any solid form and a compound X—B, wherein B is —P(O)(OR)$_2$ or —SO$_2$R, wherein R is substituted or unsubstituted $C_{1-6}$ alkyl, aralkyl or aryl, and X is halogen, to obtain a compound of Formula VIII,

FORMULA VIII

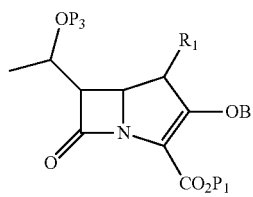

wherein $R_1$ is $C_{1-3}$ alkyl

B is —P(O)(OR)$_2$ or —SO$_2$R, wherein R is substituted or unsubstituted $C_{1-6}$ alkyl, aralkyl or aryl, $P_1$ is hydrogen or a carboxyl protecting group and $P_3$ is hydrogen or a hydroxyl protecting group, f) reacting the compound of Formula VIII with a compound of Formula IX,

HS-A  FORMULA IX

wherein A is as defined in Formula I, to obtain the compound of Formula I, and g) isolating the compound of Formula I or its stereoisomers, or salts thereof from the reaction mixture thereof.

A second aspect of the present invention provides a process for the preparation of the compound of Formula I

FORMULA I

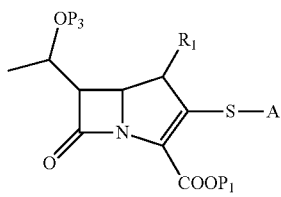

wherein
P₁ is hydrogen or a carboxyl protecting group,
P₃ is hydrogen or a hydroxyl protecting group,
R₁ is $C_{1-3}$ alkyl, and
A is selected from a group consisting of

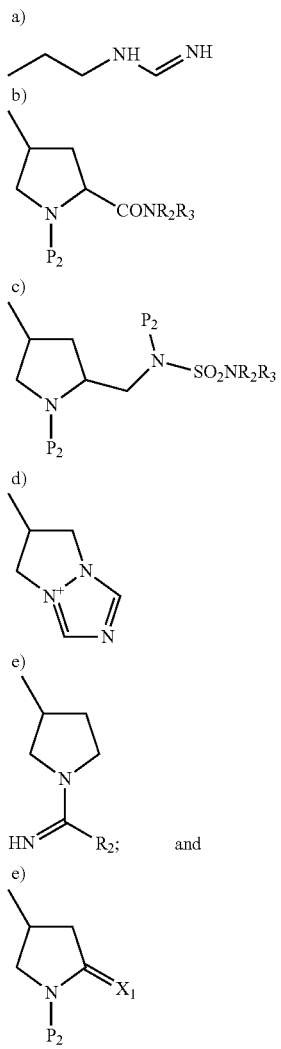

wherein
P₂ is hydrogen or an amino protecting group,
R₂ and R₃ may be same or different and are hydrogen, $C_{1-5}$ alkyl, optionally substituted aryl, or optionally substituted heteroaryl, and
X₁ is O or S,
or its stereoisomers, or salts thereof,
wherein the process comprises,
a) reacting a compound of Formula II

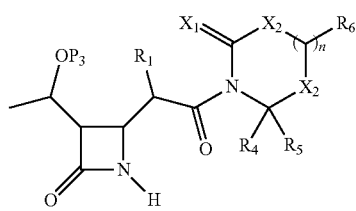

wherein
X₁ is O or S,
X₂ is O, S, NR₇ or C(R₄)R₅,
R₁ is $C_{1-3}$ alkyl,
R₄ and R₅ may be same or different and are
(i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, or
(ii) R₄ and R₅ may be joined together to form a $C_{3-18}$ cycloalkyl group, or saturated or partially unsaturated heterocycle having optionally substituted 1 to 4 ring systems, wherein each ring has 3 to 12 ring members and at least one ring member of at least one ring system is N, O or S, R₆ is
(i) hydrogen, $C_{1-18}$ alkyl, $C_{2-18}$ alkenyl, $C_{2-18}$ alkynyl, optionally substituted $C_6$-$C_1$, aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, or
(ii) R₆ may be joined together with R₄ or R₅ of X₂ to form a $C_{3-18}$ cycloalkyl group, optionally substituted $C_6$-$C_{12}$ aromatic ring or saturated or partially unsaturated heterocycle having optionally substituted 1 to 4 ring systems, wherein each ring has 3 to 12 ring members and at least one ring member of at least one ring system is N, O or S, R₇ is hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O or S, P₃ is hydrogen or a hydroxyl protecting group, and
n is 0 to 3,
and imidazole or carbonyldiimidazole in the presence of an organic solvent to obtain a compound of Formula III

FORMULA III

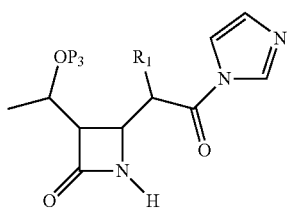

wherein
$R_1$ is $C_{1-3}$ alkyl and
$P_3$ is hydrogen or a hydroxyl protecting group,
b) reacting the compound of Formula III and a compound of Formula IV or its magnesium salt, $P_1O_2C—CH_2—CO_2H$                                FORMULA IV wherein $P_1$ is hydrogen or a carboxyl protecting group, to obtain a compound of Formula V

FORMULA V

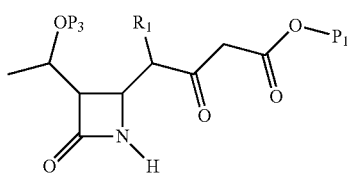

wherein
$R_1$ is $C_{1-3}$ alkyl
$P_1$ is hydrogen or a carboxyl protecting group and
$P_3$ is hydrogen or a hydroxyl protecting group,
c) reacting the compound of Formula V and an azide to obtain a compound of Formula VI,

FORMULA VI

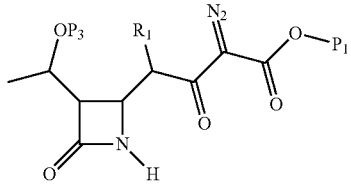

wherein $P_1$, $P_3$ and $R_1$ are as defined in Formula V,
d) cyclizing the compound of Formula VI to obtain a compound of Formula VII,

FORMULA VII

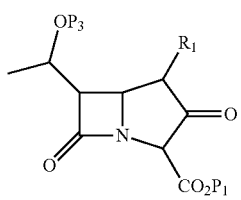

wherein $P_1$, $P_3$ and $R_1$ are as defined in Formula V,
e) reacting the compound of Formula VII and a compound X—B, wherein B is —P(O)(OR)$_2$ or —SO$_2$R, wherein R is substituted or unsubstituted $C_{1-6}$ alkyl, aralkyl or aryl, and X is halogen, to obtain a compound of Formula VIII,

FORMULA VIII

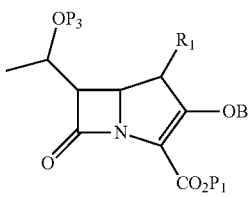

wherein
$R_1$ is $C_{1-3}$ alkyl
B is —P(O)(OR)$_2$ or —SO$_2$R, wherein R is substituted or unsubstituted $C_{1-6}$ alkyl, aralkyl or aryl,
$P_1$ is hydrogen or a carboxyl protecting group and
$P_3$ is hydrogen or a hydroxyl protecting group,
f) reacting the compound of Formula VIII with a compound of Formula IX,

HS-A                                                FORMULA IX wherein A is as defined in Formula I, to obtain the compound of Formula I, and
g) isolating the compound of Formula I or its stereoisomers, or salts thereof from the reaction mixture thereof, wherein the steps a) to g) are carried out at a temperature not more than about 45° C.

The compound of Formula II may be prepared according to the methods available in the prior art including those provided in U.S. Pat. Nos. 5,104,984; 5,792,861; 5,231,179; Japanese Patent No. 3388874, Japanese Publication Nos. 06-065195; 07-013058, EP Patent No. 0 597 423 B1, and Neera et al, *Org. Process. Res. Dev.* (2005) 9:827-829. The compound of Formula II may be, for example,

FORMULA II

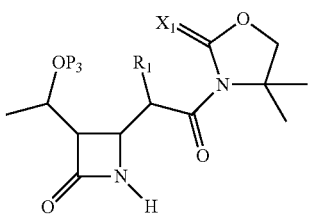

wherein
$X_1$ is O or S, $R_1$ is $C_{1-3}$ alkyl and $P_3$ is hydrogen or a hydroxyl protecting group.

The reaction of the compound of Formula II with imidazole or carbonyldiimidazole is carried out in the presence of an organic solvent and optionally a base. The organic solvent may be selected from a group consisting of aliphatic hydrocarbons, for example, hexane, heptane or pentane, halogenated hydrocarbons, for example, dichloromethane or dichloroethane, ethers, for example, diethyl ether, t-butylmethyl ether or tetrahydrofuran, esters, for example, ethyl acetate, propyl acetate, methyl acetate, isopropyl acetate or butyl acetate, aromatic hydrocarbons, for example, toluene, chlorobenzene or xylene, and a mixture thereof. The organic solvent is, for example, dichloromethane. The base may be pyridine or a pyridine derivative, for example, dialkylaminopyridine, pyrrolidinopyridine, picoline, lutidine, collidine or an alkoxypyridine. The reaction may be carried out at a temperature in the range of about 10° C. to about 40° C., for example, about 20° C. to about 30° C. The reaction may be carried out for about 10 minutes to about 100 hours, for example, about 1 hour to 3 hours. The reaction may also be followed by an optional deprotection step by base and/or acid treatment or by hydrogenation.

The compound of Formula III so obtained need not be isolated from the reaction mixture in any solid form and is directly reacted with a compound of Formula IV or its magnesium salt. The compound of Formula IV is, for example, employed as a magnesium salt, which may be obtained by treating the compound of Formula IV with magnesium halide, for example magnesium chloride. The reaction between the compound of Formula III and the compound of Formula IV or its magnesium salt may be carried out at a temperature in the range of about 10° C. to about 45° C., for example, about 20° C. to about 40° C. The reaction is carried out for about 10 minutes to about 100 hours, for example, about 1 hour to 3 hours. The reaction may also be followed by an optional deprotection step by base and/or acid treatment or by hydrogenation.

The compound of Formula V so obtained need not be isolated from the reaction mixture in any solid form. The compound of Formula V is reacted with an azide, for example, toluenesulfonylazide, methanesulfonylazide or p-carboxybenzenesulfonylazide. The reaction may be carried out in the presence of a base catalyst. The base catalyst may be triethylamine, pyridine or dimethylamine. The reaction may be carried out at a temperature in the range of about 10° C. to about 40° C., for example, about 20° C. to about 30° C. The reaction may be carried out for about 1 minute to 100 hours, for example, about 10 minutes to about 30 minutes. The reaction may also be followed by an optional deprotection step by base and/or acid treatment or by hydrogenation.

The compound of Formula VI so obtained may be isolated from the reaction or directly cyclized into the compound of Formula VII without isolation. If isolated, the reaction may be continued further in the same or different organic solvent employed in the previous steps. The organic solvent may be selected from a group consisting of aliphatic hydrocarbons, for example, hexane, heptane or pentane, halogenated hydrocarbons, for example, dichloromethane or dichloroethane, ethers, for example, diethyl ether, t-butylmethyl ether or tetrahydrofuran, esters, for example, ethyl acetate, propyl acetate, methyl acetate, isopropyl acetate or butyl acetate, aromatic hydrocarbons, for example, toluene, chlorobenzene or xylene, and a mixture thereof. The organic solvent is, for example, dichloromethane. The cyclization of the compound of Formula VI is carried out by treating the compound of Formula VI with a metal catalyst optionally in the presence of zinc halide. The metal catalyst may be a rhodium carboxylate, for example, rhodium(II)octanoate. The cyclization may be facilitated by heating the reaction mixture up to about 40° C. The reaction may also be followed by an optional deprotection step by base and/or acid treatment or by hydrogenation.

The compound of Formula VII need not be isolated from the reaction mixture in any solid form and is directly reacted with the compound X—B. The reaction of the compound of Formula VII with the compound X—B is carried out in the presence of a base. The base may be a secondary amine, for example, diisopropylamine, dicyclohexylamine, 2,2,6,6-tetramethylethylpiperidine or 1,1,3,3-tetramethylguanidine, or a tertiary amine, for example, diisopropylethylamine, triethylamine or tributylamine. The reaction may be carried out at a temperature of about 15° C. or below, for example, at a temperature in the range of about −35° to about 0° C. The formation of the compound of Formula VIII may be effected by stirring the reaction mixture. The reaction may also be followed by an optional deprotection step by base and/or acid treatment or by hydrogenation.

The compound of Formula VIII so obtained is optionally isolated from the reaction mixture. The compound of Formula VIII so obtained has a purity of about 99% or above. The compound of Formula VIII is reacted with the compound of Formula IX in the presence of an organic solvent. The compound of Formula IX may be prepared by the methods available in the prior art including those provided in U.S. Pat. Nos. 4,943,569; 4,888,344; 5,478,820; 5,317,016; 4,260,543; and 4,990,613, EP Patent No. 0 072 710 B1, and Yutaka et al, *Org. Process. Res. Dev.* (2003) 7:649-654. The reaction may be facilitated by further addition of a base. The base may be a secondary amine, for example, diisopropylamine, dicyclohexylamine, 2,2,6,6-tetramethylethylpiperidine or 1,1,3,3-tetramethylguanidine, or a tertiary amine, for example, diisopropylethylamine, triethylamine or tributylamine. The reaction may be carried out at a temperature in the range of about −35° C. to about 15° C., for example, about −20° C. to about 0° C. The reaction may be carried out for about 10 minutes to about 100 hours. The compound of Formula I so obtained may be subjected to deprotection. The deprotection may be carried out by hydrogenating the compound of Formula I in the presence of a noble metal catalyst, for example palladium—carbon. Hydrogen gas or a compound capable of generating hydrogen gas may be used as a source of hydrogen for deprotection. The compound of Formula I or its stereoisomers or salts thereof is isolated from the reaction mixture by conventional methods, for example, filtration, concentration, distillation, layer separation, solvent precipitation, reverse osmosis or a combination thereof.

While the present invention has been described in terms of its specific embodiments, certain modifications and equivalents will be apparent to those skilled in the art and are intended to be included within the scope of the present invention.

Example

Preparation of 4-Nitrobenzyl (4R,5R,6S)-3-[(Diphenoxyphosphoryl)Oxy]-6-[(1R)-1-Hydroxethyl]-4-Methyl-7-Oxo-1-Azabicyclo[3.2.0]Hept-2-Ene-2-Carboxylate (Formula VIIIA)

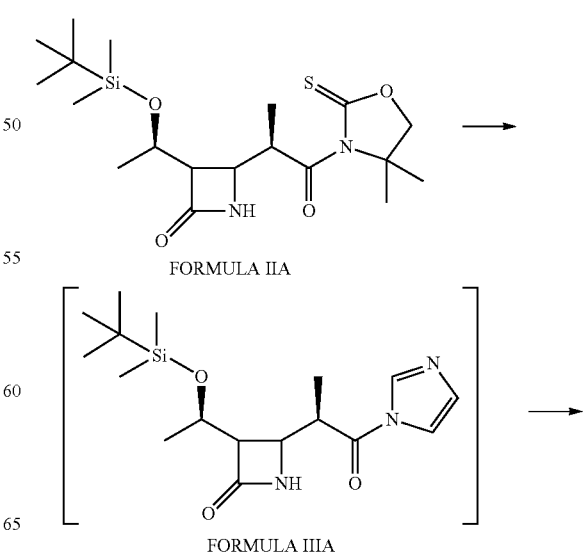

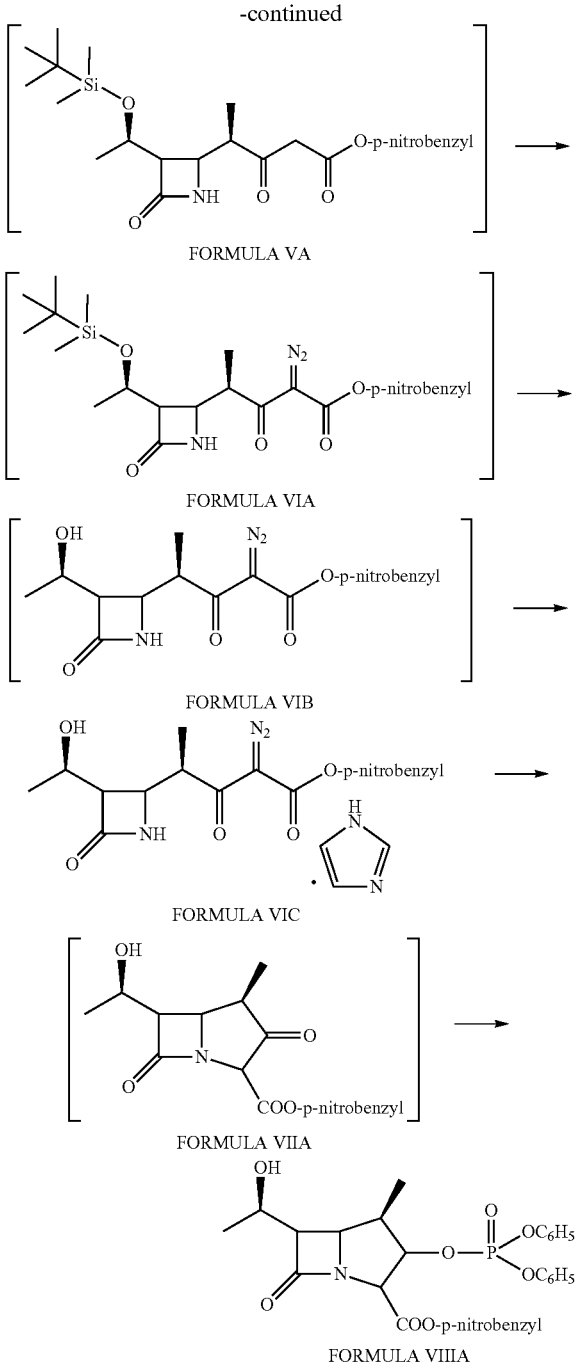

FORMULA VA

FORMULA VIA

FORMULA VIB

FORMULA VIC

FORMULA VIIA

FORMULA VIIIA

Imidazole (30 g) and dimethylaminopyridine (15 g) were added to a mixture of dichloromethane (500 mL) and the compound of Formula IIA (100 g) at 20° to 30° C. The mixture was stirred for 3 hours at 20° to 30° C. and magnesium p-nitrobenzyl malonate solution (prepared by stirring mono p-nitrobenzyl malonate (66 g) and anhydrous magnesium chloride (18 g) for 1 hour at 25° to 30° C. in the presence of dichloromethane (300 mL) and triethylamine (28 g)) was added to the reaction mixture at 25° to 30° C. The reaction mixture was refluxed for 3 hours at 40° to 45° C. and cooled to 20° to 25° C. The reaction mixture was poured into a mixture of de-mineralised water and 35% hydrochloric acid (625 mL/75 mL) at 15° to 25° C., wherein the pH of the reaction mixture was 1.5 to 3.5. The reaction mixture was stirred for 5 to 10 minutes at 15° to 20° C. and the aqueous layer was separated. 5% w/v Sodium bicarbonate solution (700 mL) was added to the organic layer and stirred for 10 minutes. The aqueous and organic layers were separated. 5% w/v sodium chloride solution (700 mL) was added to the organic layer and stirred for 10 minutes. The aqueous and organic layers were separated. Triethylamine (7.5 g) was added to the organic layer at 20° to 30° C., followed by the addition of tosylazide (52 g) in 15 to 20 minutes duration. The reaction mixture was stirred for 2 hours at 20° to 30° C. Methanol (500 mL) and 35% hydrochloric acid (90 g) were added to the reaction mixture at 20° to 30° C. The reaction mixture was stirred for 3 h at 20° to 30° C. De-mineralised water (500 mL) was added to the reaction mixture, stirred for 5 to 10 minutes at 20° to 30° C. and the layers were separated. The organic layer was washed with 5% w/v sodium bicarbonate solution (500 mL) and the layers were separated. De-mineralised water (500 mL) was added to the organic layer and the pH was adjusted to 2.0 to 3.0 with 6 N hydrochloric acid (about 5 mL). Methylene chloride was partially recovered under vacuum and isopropyl acetate (800 mL) was added to the residue. Imidazole (20 g) was added to the reaction mixture at 25° to 30° C. and stirred to obtain a solution. Seed (1 g; prepared by following the present example without the addition of seed) was added to the reaction mixture at 15° to 20° C. and stirred for 1 hour at 15° to 20° C. n-Hexane (320 mL) was added to the reaction mixture in 30 to 40 minutes at 15° to 20° C. and stirred for 6 hours at 15° to 20° C. The solid was filtered, washed with n-hexane (300 mL) and dried. The solid was suspended in dichloromethane (300 mL) and stirred to 20° to 30° C. to obtain a solution. De-mineralised water (150 mL) and 35% hydrochloric acid (20 g) were added to the solution at 20° to 30° C. The reaction mixture was stirred for 1 hour at 20° to 30° C. The organic layer was separated and washed with a mixture of de-mineralised water (150 mL) and methanol (150 mL). Dichloromethane was recovered under vacuum to obtain a residue. Dichloromethane (500 mL) was added to the residue followed by the addition of zinc bromide (0.2 g) and rhodium octanoate dimer (0.21 g). The reaction mixture was refluxed at 40° C. under stirring for 3.5 to 4.5 hours. The reaction mixture was cooled to −5° to −10° C. and diphenyl chlorophosphate (37.8 g) was added to the reaction mixture at −5° to −10° C. Dimethylaminopyridine (0.3 g) and diisopropyl ethylamine (20.25 g) were subsequently added to the reaction mixture at −5° to −10° C. and at −10° to −0° C. respectively. The reaction mixture was stirred at 0° to −5° C. for 30 to 45 minutes. Dilute hydrochloric acid (10 mL concentrated hydrochloric acid +240 mL de-ionised water) was added into the reaction mixture and the temperature was raised to 10° C. The reaction mixture was stirred for 10 minutes at 10° to 15° C. and allowed to settle for 5 to 10 minutes. The aqueous layer was separated and the organic layer was washed with de-ionised water (250 ml). Dichloromethane was recovered under vacuum and methyl isobutyl ketone (150 mL) was added to the residue. The mixture was stirred for 1 hour at 20° to 25° C., cooled to 0° to 5° C., stirred for 1 hour at 10° to 15° C. and filtered at 0° to 5° C. The solid was added to methyl isobutyl ketone (150 mL) and stirred for 1 hour at 20° to 25° C. The mixture was cooled to 0° to 5° C. and filtered at 0° to 5° C. The solid was washed with hexanes (50 mL) by passing through the solid and further washed with hexanes (150 mL) by slurrying. The solid was dried at 45° to 50° C. to obtain the title compound.

Yield: 70 g
Purity: 99.5% (HPLC)

Reference Example

Preparation of Meropenem 4-nitrobenzyl (4R,5R,6S)-3-[(diphenoxyphosphoryl)oxy]-6-[(1R)-1-hydroxyethyl]-4-methyl-7-oxo-1-azabicyclo[3.2.0]hept-2-ene-2-carboxylate (Formula VIIIA; 20 g) was dissolved in N-methyl-2-pyrrolidone (100 mL) and cooled to −20° to −15° C. 4-Nitrobenzyl (2S,4S)-2-[(dimethylamino)carbonyl]-4-mercaptopyrrolidine-1-carboxylate (12 g) was added to the reaction mixture followed by the drop-wise addition of diisopropylethylamine (5.6 g) at −15° to −5° C. and the reaction mixture was stirred. The reaction mixture was subsequently added to a buffer containing 5% palladium-carbon (30 g) and hydrogenated for 3 to 4 hours at about 25° C. (The buffer was prepared using N-methylmorpholine (3.4 g) and appropriate quantity of hydrochloric acid so as to obtain a pH of 6.5 to 7.0 in distilled water (120 mL)). The catalyst was filtered after the completion of hydrogenation and washed with water (100 mL). The filtrate was treated with activated charcoal and acetone (1.6 L) was added to the filtrate at 0° to 5° C. The reaction mixture was stirred for 6 hours at 0° to 5° C. and filtered to obtain the title compound.

Yield: 9.8 g
Purity: 98% (HPLC)

We claim:

1. A process for the preparation of a compound of Formula I

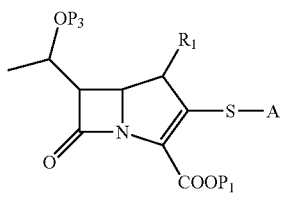

FORMULA I wherein
  $P_1$ is hydrogen or a carboxyl protecting group,
  $P_3$ is hydrogen or a hydroxyl protecting group,
  $R_1$ is a $C_{1-3}$ alkyl, and
  A is selected from the group consisting of a)
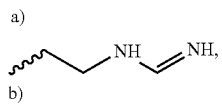

b)
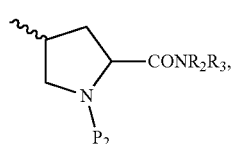

c)
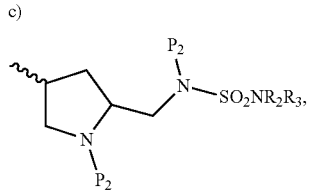

d)
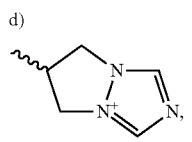

e)
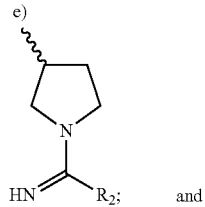   and f)
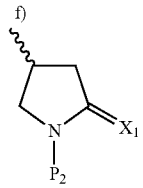

wherein
  $P_2$ is hydrogen or an amino protecting group,
  $R_2$ and $R_3$ may be the same or different and are hydrogen, $C_{1-5}$ alkyl, optionally substituted aryl, or optionally substituted heteroaryl, and
  $X_1$ is O or S,
  or its stereoisomers, or salts thereof,
the process comprising the steps of,
a) reacting a compound of Formula II

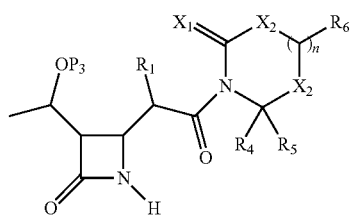

FORMULA II wherein
  $X_1$ is O or S,
  $X_2$ is O, S, $NR_7$ or $C(R_4)R_5$, provided that both $X_1$ and $X_2$ are not simultaneously S,
  $R_1$ is $C_{1-3}$ alkyl,
  $R_4$ and $R_5$ may be the same or different, and are
    (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or
    (ii) $R_4$ and $R_5$ may be joined together to form a $C_{3-18}$ cycloalkyl group, or saturated or partially unsaturated heterocycle having optionally substituted 1 to 4 ring systems, wherein each ring has 3 to 12 ring members and at least one ring member of at least one ring system is N, O, or S,
  $R_6$ is
    (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or (ii) $R_6$ may be joined together with $R_4$ or $R_5$ of $X_2$ to form a $C_{3-18}$ cycloalkyl group, optionally substituted $C_6$-$C_{12}$ aromatic ring or saturated or partially unsaturated heterocycle having optionally substituted 1 to 4 ring systems, wherein each ring has 3 to 12 ring members and at least one ring member of at least one ring system is N, O, or S, $R_7$ is hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, $P_3$ is hydrogen or a hydroxyl protecting group, and n is 0 to 3, and imidazole or carbonyldiimidazole in the presence of an organic solvent to obtain a compound of Formula III

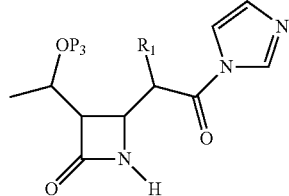

FORMULA III wherein $R_1$ is $C_{1-3}$ alkyl and $P_3$ is hydrogen or a hydroxyl protecting group, b) reacting the compound of Formula III and a compound of Formula IV or its magnesium salt, $P_1O_2C$—$CH_2$—$CO_2H$     FORMULA IV wherein $P_1$ is hydrogen or a carboxyl protecting group, to obtain a compound of Formula V

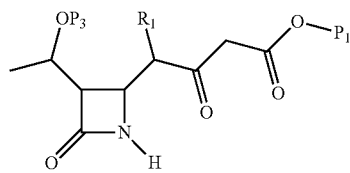

FORMULA V wherein $R_1$ is $C_{1-3}$ alkyl $P_1$ is hydrogen or a carboxyl protecting group and $P_3$ is hydrogen or a hydroxyl protecting group, c) reacting the compound of Formula V and an azide to obtain a compound of Formula VI,

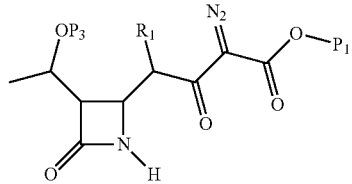

FORMULA VI wherein $P_1$, $P_3$, and $R_1$ are as defined in Formula V, d) cyclizing the compound of Formula VI to obtain a compound of Formula VII,

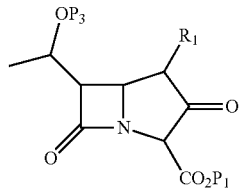

FORMULA VII wherein $P_1$, $P_3$, and $R_1$ are as defined in Formula V, e) reacting the compound of Formula VII and a compound X—B, wherein B is —P(O)(OR)$_2$ or —SO$_2$R, wherein R is substituted or unsubstituted $C_{1-6}$ alkyl, aralkyl, or aryl, and X is halogen, to obtain a compound of Formula VIII,

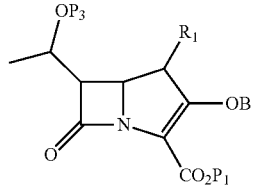

FORMULA VIII wherein $R_1$ is $C_{1-3}$ alkyl

B is —P(O)(OR)$_2$ or —SO$_2$R, wherein R is substituted or unsubstituted $C_{1-6}$ alkyl, aralkyl, or aryl, $P_1$ is hydrogen or a carboxyl protecting group and $P_3$ is hydrogen or a hydroxyl protecting group, f) reacting the compound of Formula VIII with a compound of Formula IX

HS-A     FORMULA IX wherein A is as defined in Formula I, to obtain a compound of Formula I, and g) isolating the compound of Formula I or its stereoisomers, or salts thereof from the reaction mixture, wherein the compounds of Formula III, VI, and VII are not isolated from the reaction mixture in solid form during the process.

2. A process for the preparation of a compound of Formula I

FORMULA I

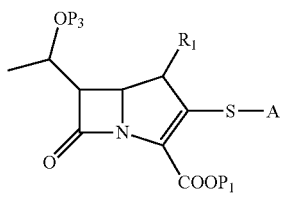

wherein
P₁ is hydrogen or a carboxyl protecting group,
P₃ is hydrogen or a hydroxyl protecting group,
R₁ is a $C_{1-3}$ alkyl, and
A is selected from the group consisting of a)
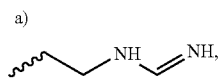

b)
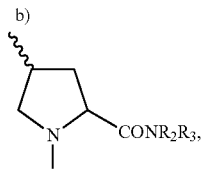

c)
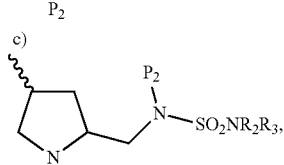

d)
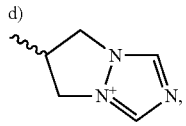

e)
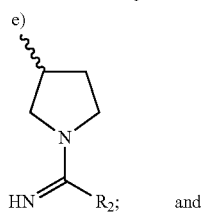    and f)
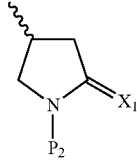

wherein
P₂ is hydrogen or an amino protecting group,
R₂ and R₃ may be the same or different and are hydrogen, $C_{1-5}$ alkyl, optionally substituted aryl, or optionally substituted heteroaryl, and
X₁ is O or S,
or its stereoisomers, or salts thereof, wherein the process comprises,
a) reacting a compound of Formula II

FORMULA II

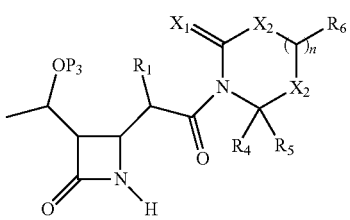

wherein
X₁ is O or S,
X₂ is O, S, NR₇, or C(R₄)R₅, provided that both X₁ and X₂ are not simultaneously S,
R₁ is $C_{1-3}$ alkyl,
R₄ and R₅ may be the same or different, and are
(i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or
(ii) R₄ and R₅ may be joined together to form a $C_{3-18}$ cycloalkyl group, or saturated or partially unsaturated heterocycle having optionally substituted 1 to 4 ring systems, wherein each ring has 3 to 12 ring members and at least one ring member of at least one ring system is N, O, or S,
R₆ is
(i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or
(ii) R₆ may be joined together with R₄ or R₅ of X₂ to form a $C_{3-18}$ cycloalkyl group, optionally substituted $C_6$-$C_{12}$ aromatic ring or saturated or partially unsaturated heterocycle having optionally substituted 1 to 4 ring systems, wherein each ring has 3 to 12 ring members and at least one ring member of at least one ring system is N, O, or S,
R₇ is hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S,
P₃ is hydrogen or a hydroxyl protecting group, and
n is 0 to 3,
and imidazole or carbonyldiimidazole in the presence of an organic solvent to obtain a compound of Formula III

FORMULA III

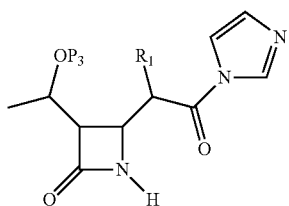

wherein
R$_1$ is C$_{1-3}$ alkyl and
P$_3$ is hydrogen or a hydroxyl protecting group,
b) reacting the compound of Formula III and a compound of Formula IV or its magnesium salt,

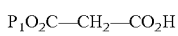     FORMULA IV wherein P$_1$ is hydrogen or a carboxyl protecting group, to obtain a compound of Formula V

FORMULA V

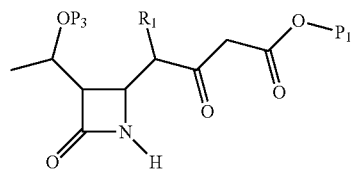

wherein
R$_1$ is C$_{1-3}$ alkyl
P$_1$ is hydrogen or a carboxyl protecting group and
P$_3$ is hydrogen or a hydroxyl protecting group,
c) reacting the compound of Formula V and an azide to obtain a compound of Formula VI,

FORMULA VI

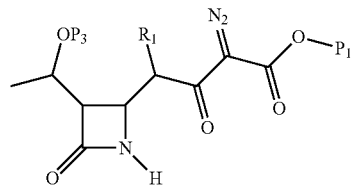

wherein P$_1$, P$_3$, and R$_1$ are as defined in Formula V,
d) cyclizing the compound of Formula VI to obtain a compound of Formula VII,

FORMULA VII

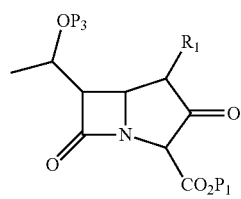

wherein P$_1$, P$_3$, and R$_1$ are as defined in Formula V,
e) reacting the compound of Formula VII and a compound X—B, wherein B is —P(O)(OR)$_2$ or —SO$_2$R, R is substituted or unsubstituted C$_{1-6}$ alkyl, aralkyl, or aryl, and X is halogen, to obtain a compound of Formula VIII,

FORMULA VIII

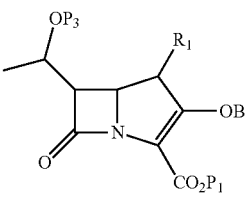

wherein
R$_1$ is C$_{1-3}$ alkyl
B is —P(O)(OR)$_2$ or —SO$_2$R, wherein R is substituted or unsubstituted C$_{1-6}$ alkyl, aralkyl, or aryl,
P$_1$ is hydrogen or a carboxyl protecting group and
P$_3$ is hydrogen or a hydroxyl protecting group,
f) reacting the compound of Formula VIII with a compound of Formula IX,

HS-A     FORMULA IX wherein A is as defined in Formula I, to obtain a compound of Formula I, and
g) isolating the compound of Formula I or its stereoisomers, or salts thereof from the reaction mixture,
wherein the compounds of Formula III, VI, and VII are not isolated from the reaction mixture in solid form during the process, and wherein the steps a) to g) are carried out at a temperature not more than 45° C.

3. The process according to claim 1 or 2, wherein the organic solvent in step a) is selected from the group consisting of aliphatic hydrocarbons, halogenated hydrocarbons, ethers, esters, aromatic hydrocarbons, and a mixture thereof.

4. The process according to claim 3, wherein the halogenated hydrocarbon is dichloromethane.

5. The process according to claim 1 or 2, wherein step a) is carried out in the presence of a base.

6. The process according to claim 5, wherein the base is selected from pyridine, dialkylaminopyridine, pyrrolidinopyridine, picoline, lutidine, collidine, or an alkoxypyridine.

7. The process according to claim 1 or 2, wherein the azide in step c) is selected from toluenesulfonylazide, methanesulfonylazide, or p-carboxybenzenesulfonylazide.

8. A process for the preparation of a compound of Formula VIII having a purity of at least 99%

FORMULA VIII

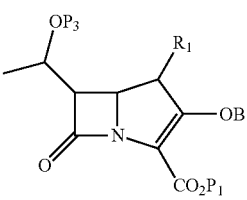

wherein
R$_1$ is a C$_{1-3}$ alkyl,
B is —P(O)(OR)$_2$ or —SO$_2$R, wherein R is substituted or unsubstituted C$_{1-6}$ alkyl, aralkyl, or aryl group,
P$_1$ is hydrogen or a carboxyl protecting group, and
P$_3$ is hydrogen or a hydroxyl protecting group, wherein the process comprises, a) reacting a compound of Formula II

FORMULA II wherein $X_1$ is O or S, $X_2$ is O, S, $NR_7$, or $C(R_4)R_5$, provided that both $X_1$ and $X_2$ are not simultaneously S, $R_1$ is $C_{1-3}$ alkyl, $R_4$ and $R_5$ may be the same or different, and are (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or (ii) $R_4$ and $R_5$ may be joined together to form a $C_{3-18}$ cycloalkyl group, or saturated or partially unsaturated heterocycle having optionally substituted 1 to 4 ring systems, wherein each ring has 3 to 12 ring members and at least one ring member of at least one ring system is N, O, or S, $R_6$ is (i) hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, or (ii) $R_6$ may be joined together with $R_4$ or $R_5$ of $X_2$ to form a $C_{3-18}$ cycloalkyl group, optionally substituted $C_6$-$C_{12}$ aromatic ring or saturated or partially unsaturated heterocycle having optionally substituted 1 to 4 ring systems, wherein each ring has 3 to 12 ring members and at least one ring member of at least one ring system is N, O, or S, $R_7$ is hydrogen, $C_{1-18}$ alkyl, $C_{2-18}$ alkenyl, $C_{2-18}$ alkynyl, optionally substituted $C_6$-$C_{12}$ aryl, optionally substituted $C_7$-$C_{19}$ aralkyl, $C_{3-18}$ cycloalkyl, or saturated or partially unsaturated heterocyclyl or heterocyclylalkyl having optionally substituted 1 to 4 ring systems, wherein each ring has 3 to 12 ring members and at least one ring member of at least one ring system is N, O, or S, $P_3$ is hydrogen or a hydroxyl protecting group, and n is 0 to 3, and imidazole or carbonyldiimidazole in the presence of an organic solvent to obtain a compound of Formula III

FORMULA III wherein $R_1$ is $C_{1-3}$ alkyl and $P_3$ is hydrogen or a hydroxyl protecting group, b) reacting the compound of Formula III and a compound of Formula IV or its magnesium salt, $P_1O_2C-CH_2-CO_2H$   FORMULA IV wherein $P_1$ is hydrogen or a carboxyl protecting group, to obtain a compound of Formula V

FORMULA V wherein $R_1$ is $C_{1-3}$ alkyl $P_1$ is hydrogen or a carboxyl protecting group and $P_3$ is hydrogen or a hydroxyl protecting group, c) reacting the compound of Formula V and an azide to obtain a compound of Formula VI,

FORMULA VI wherein $P_1$, $P_3$, and $R_1$ are as defined in Formula V, d) cyclizing the compound of Formula VI to obtain a compound of Formula VII,

FORMULA VII wherein $P_1$, $P_3$, and $R_1$ are as defined in Formula V, e) reacting the compound of Formula VII and a compound X—B, wherein B is —P(O)(OR)$_2$ or —SO$_2$R, wherein R is substituted or unsubstituted $C_{1-6}$ alkyl, aralkyl, or aryl, and X is halogen, to obtain a compound of Formula VIII, wherein the compounds of Formula III, VI, and VII are not isolated from the reaction mixture in solid form during the process.

* * * * *

UNITED STATES PATENT AND TRADEMARK OFFICE
CERTIFICATE OF CORRECTION

PATENT NO.        : 8,841,444 B2
APPLICATION NO.   : 13/056837
DATED             : September 23, 2014
INVENTOR(S)       : Neera Tewari et al.

It is certified that error appears in the above-identified patent and that said Letters Patent is hereby corrected as shown below:

In the Specification

COLUMN 2, LINE 25: "EP Patent No. 0 300 657131," should read -- EP Patent No. 0 300 657 B1, --

COLUMN 2, LINES 37 and 38: "Heterocycles, (1995) 36:145-159" should read -- Heterocycles, (1995) 41:147-159 --

COLUMN 7, LINE 1: "(ii) $R_6$ may be joined together with $R_1$ or $R_5$ of $X_2$ to form" should read -- "(ii) $R_6$ may be joined together with $R_4$ or $R_5$ of $X_2$ to form --

COLUMN 7, LINE 8: "$R_7$ is hydrogen, $C_{1-18}$ alkyl, $C_{2-48}$ alkenyl, $C_{2-18}$ alkynyl," should read -- $R_7$ is hydrogen, $C_{1-18}$ alkyl, $C_{2-18}$ alkenyl, $C_{2-18}$ alkynyl, --

COLUMN 9, LINES 51-52:

should read --

COLUMN 10, LINE 40: "optionally substituted $C_6$-$C_1$, aryl," should read -- optionally substituted $C_6$-$C_{12}$ aryl, --

Signed and Sealed this
Twenty-ninth Day of September, 2015

Michelle K. Lee
*Director of the United States Patent and Trademark Office*